United States Patent [19]

Bucsh et al.

[11] Patent Number: 5,514,812

[45] Date of Patent: May 7, 1996

[54] PREPARATION OF STEREOCHEMICALLY PURE OXIMES WITH MUSCARINIC ACTIVITY

[75] Inventors: Ruth Bucsh, Canton; Juan C. Jaen, Plymouth, both of Mich.; Edgardo Laborde, Lincoln University, Pa.; Anthony J. Thomas, Ann Arbor, Mich.

[73] Assignee: Warner-Lambert Company, Morris Plains, N.J.

[21] Appl. No.: 257,858

[22] Filed: Jun. 10, 1994

[51] Int. Cl.⁶ .................................................. C07D 487/08
[52] U.S. Cl. .......................... 548/452; 548/128; 548/131; 546/238; 546/272; 544/143; 544/212; 544/373
[58] Field of Search ...................... 548/453, 128, 548/131; 546/238, 272; 544/143, 212, 373

[56] References Cited

U.S. PATENT DOCUMENTS

| | | | |
|---|---|---|---|
| 3,004,979 | 10/1961 | Riehen et al. | 260/294.8 |
| 4,158,015 | 6/1979 | Paul | 260/566 A |
| 4,710,508 | 12/1987 | Bergmeier et al. | 514/357 |
| 5,306,718 | 4/1994 | Lauffer et al. | 514/230.8 |
| 5,318,978 | 6/1994 | Lauffer et al. | 514/299 |

FOREIGN PATENT DOCUMENTS

| | | |
|---|---|---|
| 445731A1 | 9/1991 | European Pat. Off. . |
| 2086292 | 12/1971 | France . |
| 2258652 | 2/1993 | United Kingdom . |
| 93/08191 | 4/1993 | WIPO . |

OTHER PUBLICATIONS

Davies, P., et al., *Lancet*, 1976, 2, 1403.
Perry, E. K., et al., *J Neurological Sciences*, 1977, 34, 247–265.
White, P., et al., *Lancet*, 1977, 668–670.
Peterson, C., et al., *Neurobiology of Aging*, 1984, 4, 25–30.
Davis, H. P., et al., *Experimental Aging Research*, 1983, 9:3, 211–214.
Christie, J. E., et al., *Brit J. Psychiat*, 1981, 138, 46–50.
Hollander, E., et al., *British Medical Bulletin*, 1986, 42:1, 97–100.
Bonner, T. I., *Trends Pharmacol Sci*, 1989, Supplement on Subtypes of Muscarinic Receptors IV, 11–15.
Ibe, B. O., *Univ Microfilms Int*, 1984, *Diss. Abstr. Int. B*, 45(7), 2120, 271 pages.

*Primary Examiner*—David B. Springer
*Attorney, Agent, or Firm*—Elizabeth M. Anderson

[57] ABSTRACT

The instant invention is a selective formation of the Z-oxime and O-alkylation of 1-azabicyclo[2.2.1]heptan-3-one and 1-azabicyclo[2.2.2]heptan-3-one oximes to produce compounds with muscarinic activity. The process is capable of scale-up for industrial purposes as it provides better yields and ease of preparation. Intermediates are also described.

5 Claims, No Drawings

PREPARATION OF STEREOCHEMICALLY PURE OXIMES WITH MUSCARINIC ACTIVITY

BACKGROUND OF THE INVENTION

Disorders of cognition are generally characterized by symptoms of forgetfulness, confusion, memory loss, attentional deficits, and/or, in some cases, affective disturbances. These symptoms may arise as a result of the general aging process and/or from organic brain disease, cerebrovascular disease, head injury, or developmental or genetic defects.

The general decrease in cognitive function which accompanies the aging process is well accepted. The same phenomenon has been observed and documented in many lower mammals, including those routinely employed in pharmacological testing programs for screening and predicting usefulness for particular drugs in higher animals, including humans.

Although disorders of cognition often accompany the general aging process, presenile and senile primary degenerative dementia are the most common accepted causes of mental deterioration in the elderly. It has been estimated that at least 10 percent of persons over 60 years of age will eventually suffer severe mental deterioration. A much larger number will experience cognitive decline of sufficient severity to impede their activities.

Many of the symptoms of cognitive disorders, especially impaired memory, are associated with decreased acetylcholine synthesis and the impairment of cholinoreceptive neurons. In the hippocampus and cerebral cortex of patients suffering from primary degenerative dementia, for example, the level of the enzyme choline acetyltransferase (CAT) can be reduced by as much as 90% (see Davies, et al., *The Lancet* 1976;2:1403; Perry, et al., *J. Neurol. Sci.* 1977;34:247–265; and White, et al., *The Lancet* 1977;1:668–670).

Since CAT catalyzes the synthesis of acetylcholine from its precursors choline and acetyl coenzyme A, the loss of CAT reflects the loss of cholinergic, or acetylcholine-releasing, nerve endings in the hippocampus and cerebral cortex. There is abundant evidence that cholinergic terminals in the hippocampus are critically important for memory formation.

The cholinergic hypothesis suggests that drugs which restore acetylcholine levels or which mimic the action of acetylcholine (i.e., are cholinomimetic) are effective in correcting this deficit in neurotransmitter chemical and provide treatment of the memory impairment symptom of cerebral insufficiency. Considerable biochemical, pharmacological, and electrophysiological evidence supports the hypothesis that deficits in the cholinergic system underlie geriatric cognitive dysfunction (see Peterson C., Gibson G. E., *Neurobiol. Aging* 1983;4:25–30). Aged humans and nonhuman primates with decreased cognition show improved memory when they are treated, for example, with acetylcholinesterase inhibitors such as physostigmine. These agents increase the available supply of synaptic acetylcholine by inhibiting its hydrolysis.

Aminopyridines such as 3,4-diaminopyridine ameliorate age-related cognitive deficits by increasing the release of acetylcholine from presynaptic nerve terminals, thus increasing synaptic acetylcholine (see Davis HP, et al., *Exp. Aging Res.* 1983;9:211–214).

It has been known for some time that the natural alkaloid, muscarine, has the ability to act relatively selectively at autonomic effector cells to produce qualitatively the same effects as acetylcholine. Two alkaloids, pilocarpine and arecoline (the methyl ester of 1,2,5,6-tetrahydro-1-methyl-3-pyridinecarboxylic acid), have the same principal sites of action as muscarine and acetylcholine and are thus classified as having "muscarinic" action. Although these naturally occurring alkaloids are of great value as pharmacological tools, present clinical use is largely restricted to the use of pilocarpine as a miotic agent.

Recently it has been demonstrated that arecoline is effective in ameliorating some of the symptoms of cognitive disorders in patients clinically diagnosed as having presenile primary degenerative dementia. Significant improvement was observed in a test of picture recognition after administration of arecoline to patients in a double-blind study (see Christie, et al., *Brit. J. Psychiatry* 1981;138:46–50).

The use of cholinomimetic agents in multiple clinical trials has documented both the potential therapeutic utility of cholinergic agents and the high incidence of unwanted side effects (see Hollander E., et al., *Brit. Med. Bull.* 1986;42:97–100). Many of these unwanted side effects result from the nonselective stimulation of cholinergic receptors (of the muscarinic type) located throughout the body. Muscarinic receptors have been classified pharmacologically and at the molecular level into several subtypes (see Bonner T., *Trends Pharmacol. Sci.* 1989;(Suppl. on Subtypes of Muscarinic Receptors IV):11–15). The receptors responsible for the central cognition-enhancing effects of muscarinic cholinomimetic agents are generally defined as $M_1$ (pharmacological definition) or m1 (molecular definition). Activation of peripheral $M_2$ and $M_3$ (or m2 and m3) receptors is thought to be responsible for the unwanted side effects of the currently available muscarinic agents (e.g., sweating, diarrhea, cramps, excessive salivation, etc). Thus, selective $M_1$ (or m1) muscarinic agonists hold the best promise for selective improvement of cognitive function without the occurrence of unwanted side effects.

U.S. Pat. No. 5,306,718 covers final products prepared by the process of the instant invention.

A continuation-in-part application, U.S. Ser. No. 08/110,904 filed Aug. 24, 1993, is pending. Both of these are incorporated by reference.

Certain 3- or 4-ketoximes of 1-(lower alkyl)- 1,2,5,6-tetrahydropyridines in which the oxygen is unsubstituted are disclosed in U.S. Pat. No. 3,004,979, having utility as parasympathomimetic agents acting on nonstriated muscle.

U.S. Pat. No. 4,710,508 describes O-substituted 1-(1,2,3,6-tetrahydro-1-methyl- 3-pyridinyl)ketone oximes and O-substituted 1-(1,2,3,6-tetrahydro-4-pyridinyl)ketone oximes which are useful as analgesic agents or agents for the treatment of the symptoms of cerebral insufficiency characterized by decreased central acetylcholine production.

Dissertation Abstracts Int. B 1984;45(7):2120; CA102:113440m describes oxime-O-ethers of the following formula as having anticholinergic properties:

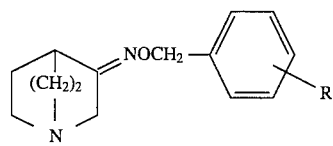

wherein R is F, Cl, Br, $NO_2$, $OCH_3$, $CF_3$, or $CH_3$. Particularly relevant are pages 128–136, 166, 167, 198–203.

French Patent Number 2,086,292 describes 3-quinuclidinone oxime carbamates of the following formula having insecticidal and acaricidal activity.

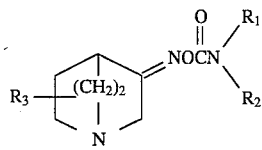

wherein $R_3$ is alkyl, alkenyl, alkylidene, halogen, cyano, haloalkyl, haloalkenyl, alkoxy, etc; $R_1$ and $R_2$ are hydrogen, lower alkyl, acyl which may be substituted, lower alkenyl, or the group R—O—CH$_2$— wherein R is methyl, ethyl, isopropyl; propyl-1,2-diene, allyl, 1-methyl-2-propenyl; phenyl or benzyl.

British Patent Application 2,258,652 covers azabicyclic oxime ether derivatives which are taught to be useful in stimulating muscarinic acetylcholine receptors. The compounds are represented by the formula

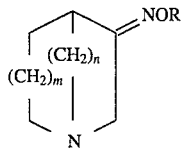

wherein R is an alkyl of from 1 to 6.

U.S. Pat. No. 4,158,015 teaches a process for the stereoselective synthesis of the E-isomer of certain aryl alkyl ketoximes useful as insecticidals. The oximes are formed as a mixture of isomers and the mixture was isomerized with acid catalysis. The compounds are of the type

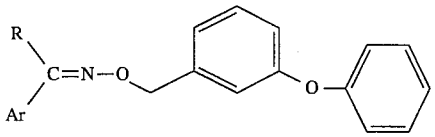

wherein R is alkyl, cycloalkyl, alkenyl, any of which can be substituted by halogen, hydroxy, alkoxy, alkylsulfonyl, cyano, nitro, carboalkoxy, or acyl. The process discussed does not work in the present invention to prepare the desired pure Z-oxime.

SUMMARY OF THE INVENTION

The instant invention is an alkylation process for the preparation of compounds of Formula I

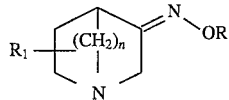

wherein R, $R_1$, and n are as described below.

DETAILED DESCRIPTION

The azabicyclo[2.2.1]heptan-3-one oxime and azabicyclo[2.2.2]octan-3-one oxime compounds of Formula I can exist in two possible geometric forms known as E- and Z-. The pharmacological activity resides in the Z-isomers (U.S. Pat. No. 5,306,718). The compounds have proved to be hard to separate on a small scale and not possible to separate on a large scale. The mixtures are partially separated by medium pressure chromatography. The low yield and the difficulty of separation were problems in the preparation of the final products.

Unexpectedly, the instant process has overcome these problems and the process is expected to find utility in manufacturing plants on a larger scale. Only two steps are required and a good yield is produced.

The compounds prepared by the novel process of the instant invention are those of formula

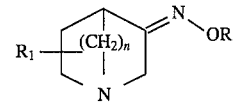

or a pharmaceutically acceptable acid addition salt thereof and includes racemic as well as enantiomerically pure forms and mixtures thereof
wherein n is an integer from 1 to 2;

$R_1$ is hydrogen, a straight or branched lower alkyl group of from 1 to 6 carbon atoms, hydroxy, a straight or branched lower alkoxy group of from 1 to 4 carbon atoms, acyloxy group wherein the acyl moiety has from 2 to 5 carbon atoms, or the group —(CH$_2$)$_m$NR$_{11}$R$_{12}$ wherein m is an integer of from 0 to 4 and R$_{11}$ and R$_{12}$ are the same or different and are hydrogen, a straight or branched lower alkyl of from 1 to 4 carbon atoms, or R$_{11}$ and R$_{12}$ can form a ring of from 3 to 6 atoms;

R is (a) hydrogen;

(b) a straight or branched hydrocarbon chain having from 1 to 20 carbon atoms which is saturated or which is unsaturated and contains from 1 to 4 double and/or triple bonds;

(c) a straight or branched hydrocarbon chain having from 1 to 20 carbon atoms which is saturated or which is unsaturated and contains from 1 to 4 double and/or triple bonds, and the terminal carbon of the hydrocarbon chain is substituted with a group selected from:

(i) a cycloalkyl group having from 3 to 8 carbon atoms or a cycloalkenyl group having from 4 to 8 carbon atoms;

(ii) an aromatic group selected from phenoxy, phenyl, 2- or 3-thienyl, 2- or 3-furanyl, 2- or 3-pyrrolyl, 2-, 3-, or 4-pyridinyl, 3- or 5-(1,2,4)-thiadiazolyl, 3-(1,2,5)-thiadiazolyl, 2-(1,3,4)-thiadiazolyl, 2-triazinyl, 3- or 5-(1,2,4)-oxadiazolyl, 2-(1,3,4)-oxadiazolyl, 3-(1,2,5)-oxadiazolyl, 3- or 5-thiadiazolyl, 2- or 5-pyrimidinyl, 3- or 4-pyridazinyl, 2-, 4-, or 5-thiazolyl, 2-, 4-, or 5-oxazolyl, or 2-pyrazinyl wherein the aromatic group is unsubstituted or is substituted with 1 or 2 substituents selected from straight or branched alkyl having from 1 to 4 carbon atoms, straight or branched alkoxy having from 1 to 4 carbon atoms, chlorine, fluorine, bromine, trifluoromethyl, nitro, hydroxy, trifluoromethoxy, or NR$_4$R$_5$ wherein R$_4$ and R$_5$ have the meanings defined above, (iii) —NR$_6$R$_7$
wherein each of R$_6$ and R$_7$ is hydrogen, alkyl having from 1 to 4 carbon atoms, phenyl or benzyl, or —NR$_6$R$_7$ taken together form a pyrrolidino, piperidino, piperazino, or morpholino ring;

(iv)

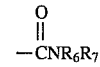

wherein R$_6$ and R$_7$ have the meanings defined above;

(v)

wherein $R_8$ is a straight or branched alkyl group having from 1 to 6 carbon atoms;

(vi) CN;

(vii) —$CO_2R_9$ wherein $R_9$ is hydrogen, a straight or branched hydrocarbon group having from 1 to 6 carbon atoms which is saturated or which is unsaturated and contains 1 or 2 double and/or triple bonds, or benzyl;

(viii) $XR_{10}$ wherein X is oxygen or sulfur, and $R_{10}$ is a straight or branched hydrocarbon chain having from 1 to 6 carbon atoms which is saturated or which is unsaturated and contains 1 or 2 double and/or triple bonds and is unsubstituted or is substituted with an alkoxy group having from 1 to 4 carbon atoms;

(ix) biphenyl;

(d) the group —$CH_2CH_2CH$=$C(Ph)_2$; or (e) the group

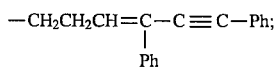

comprising:

(a) stirring a mixture of 1-azabicyclo[2.2.1]heptan-3-one (U.S. Pat. No. 5,306,718) or 1-azabicyclo [2.2.2]octan-3-one (commercially available) or a salt thereof, and hydroxylamine, or a salt thereof, in an alcohol solvent of sufficient dilution to keep reactants and products in solution at a temperature of from 0° C. to 24° C. for from 2 to 48 hours;

(b) removing the solvent, dissolving the remaining product, neutralizing it with base, extracting into an organic solvent, and drying it to produce the stereochemically pure Z-oxime;

(c) adding the Z-oxime in portions to a suspension of a base with a mono- or dibasic counterion in an aprotic solvent with stirring for from 5 minutes to 5 hours from 0° C. to 50° C. producing the corresponding oxime anion;

(d) adding the product of Step (c) above to a solution of an alkylating agent of Formula R—X, where R is as defined above, and X is a leaving group, in an inert solvent and stirring the mixture at a temperature of from −78° C. to 78° C. for from 10 minutes to 48 hours;

(e) quenching the reaction, removing the solvent and filtering through silica gel to provide the desired specific oxime Z-isomer of Formula I.

Preferred compounds of the present invention are those of Formula I:

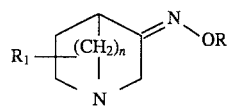

or a pharmaceutically acceptable acid addition salt thereof wherein n is 1;

$R_1$ is hydrogen;

R is a straight or branched hydrocarbon chain of from 1 to 20 atoms which chain is saturated or unsaturated and has from 1 to 4 double and/or triple bonds, and the terminal carbon is substituted by an aromatic group selected from phenoxy, phenyl, 2- or 3-thienyl, 2- or 3-furanyl, 2- or 3-pyrrolyl, 2-, 3-, or 4-pyridinyl, 3- or 5-(1,2,4)-thiadiazolyl, 3-(1,2,5)-thiadiazolyl, 2-(1,3,4)-thiadiazolyl, 2-triazinyl, 3- or 5-(1,2,4)-oxadiazolyl, 2-(1,3,4)-oxadiazolyl, 3-(1,2,5)-oxadiazolyl, 3- or 5-thiadiazolyl, 2- or 5-pyrimidinyl, 3- or 4-pyridazinyl, 2-, 4-, or 5-thiazolyl, 2-, 4-, or 5-oxazolyl, or 2-pyrazinyl wherein the aromatic group is unsubstituted or is substituted with 1 or 2 substituents selected from straight or branched alkyl having from 1 to 4 carbon atoms, straight or branched alkoxy having from 1 to 4 carbon atoms, chlorine, fluorine, bromine, trifluoromethyl, nitro, hydroxy, trifluoromethoxy, or $NR_4R_5$ wherein $R_4$ and $R_5$ have the meanings defined above, comprising:

(a) stirring a mixture of 1-azabicyclo[2.2.1]heptan-3-one or 1-azabicyclo[2.2.2]octan-3-one hydrochloride and hydroxylamine hydrochloride in an alcohol solvent of sufficient dilution to keep reactants and products in solution at a temperature of from 0° C. to 24° C. for from 2 to 48 hours;

(b) removing the solvent, dissolving the remaining product, neutralizing it with base, extracting it into an organic solvent, and drying the extract to produce the stereochemically pure Z-oxime;

(c) adding the oxime in portions to a suspension of potassium hydride or potassium tert-butoxide or potassium bis(trimethylsilyl)amide in DMF or THF with stirring for from 10 minutes to 2 hours at 0° C. to 30° C. producing the desired oxime anion;

(d) adding the product of Step (c) to a solution of R—X, where R is as defined above and X is $OSO_2Ar$ or Br in an inert solvent and stirring the mixture at −10° C. to 50° C. for from 0.5 hour to 18 hours;

(e) quenching the reaction, removing the solvent and filtering through silica gel to provide the desired specific oxime Z-isomer of Formula I.

More preferably, the present invention is directed to compounds of Formula I and pharmaceutically acceptable salts thereof,

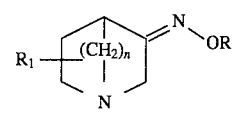

wherein n is 1;

$R_1$ is hydrogen;

R is a straight or branched hydrocarbon chain of from 1 to 8 atoms which chain contains from 1 to 2 double or triple bonds, and the terminal carbon is substituted by an aromatic group selected from phenyl, 2- or 3-thienyl, 2- or 3-furanyl, 2-, 3-, or 4-pyridinyl, 2-, 4-, or 5-thiazolyl, or 2-, 4-, or 5-oxazolyl, wherein the aromatic group is unsubstituted or substituted with 1 or 2 substituents selected from straight or branched alkyl having from 1 to 4 carbon atoms, straight or branched alkoxy having from 1 to 4 carbon atoms, chlorine, bromine, fluorine, trifluoromethyl, nitro, hydroxy, trifluoromethoxy, or $NR_4R_5$ wherein $R_4$ and $R_5$ have the meanings defined above; comprising:

(a) stirring a mixture of 1-azabicyclo[2.2.1]heptan- 3-one or 1-azabicyclo[2.2.2]octan-3-one hydrochloride and hydroxylamine hydrochloride in methanol or ethanol at a concentration of ≦0.4M at a temperature of from 0° C. to 24° C. for from 2 to 48 hours;

(b) removing the solvent and dissolving the remaining product in water, increasing the pH with carbonate, and extracting the organic product into CHCl₃ and drying the extract to produce the unsubstituted Z-oxime (Formula I, R=H);

(c) adding the Z-oxime of Formula I (R=H) in portions to a suspension of potassium hydride or potassium bis (trimethylsilyl) amide or potassium tert-butoxide in DMF or THF with stirring for from 15 minutes to 1 hour at room temperature producing the corresponding oxime anion of Formula I (R=K);

(d) adding the crude reaction mixture from Step (c) to a solution of a compound of Formula R—X, wherein R is as defined above and X is —OSO₂—(p—Me—C₆H₄) or bromine in DMF or THF and stirring the mixture at 0° C. to 30° C. for from 1 to 2 hours;

(e) quenching the reaction and removing the solvent, and filtering through silica gel to provide a compound of Formula I selected from:

Z-(±)-1-Azabicyclo[2.2.1]heptan-3-one, O-(3-(2'-methoxyphenyl)-2-propynyl)oxime;
Z-(+)-1-Azabicyclo[2.2.1]heptan-3-one, O-(3-(2'-methoxyphenyl)-2-propynyl)oxime;
Z-(−)-1-Azabicyclo[2.2.1]heptan-3-one, O-(3-(2'-methoxyphenyl)-2-propynyl)oxime;
Z-(±)-1-Azabicyclo[2.2.1]heptan-3-one, O-(3-(4'-methoxyphenyl)-2-propynyl)oxime;
Z-(+)-1-Azabicyclo[2.2.1]heptan-3-one, O-(3-(4'-methoxyphenyl)-2-propynyl)oxime;
Z-(−)-1-Azabicyclo[2.2.1]heptan-3-one, O-(3-(4'-methoxyphenyl)-2-propynyl)oxime;
Z-(±)-1-Azabicyclo[2.2.1]heptan-3-one, O-(3-(3'-methoxyphenyl)-2-propynyl)oxime;
Z-(+)-1-Azabicyclo[2.2.1]heptan-3-one, O-(3-(3'-methoxyphenyl)-2-propynyl)oxime;
Z-(−)-1-Azabicyclo[2.2.1]heptan-3-one, O-(3-(3'-methoxyphenyl)-2-propynyl)oxime;
Z-(±)-1-Azabicyclo[2.2.1]heptan-3-one, O-(3-(2'-chlorophenyl)-2-propynyl)oxime;
Z-(+)-1-Azabicyclo[2.2.1]heptan-3-one, O-(3-(2'-chlorophenyl)-2-propynyl)oxime;
Z-(−)-1-Azabicyclo[2.2.1]heptan-3-one, O-(3-(2'-chlorophenyl)-2-propynyl)oxime;
Z-(±)-1-Azabicyclo[2.2.1]heptan-3-one, O-(3-(3'-chlorophenyl)-2-propynyl)oxime;
Z-(+)-1-Azabicyclo[2.2.1]heptan-3-one, O-(3-(3'-chlorophenyl)-2-propynyl)oxime;
Z-(−)-1-Azabicyclo[2.2.1]heptan-3-one, O-(3-(3'-chlorophenyl)-2-propynyl)oxime;
Z-(±)-1-Azabicyclo[2.2.1]heptan-3-one, O-(3-(4'-chlorophenyl)-2-propynyl)oxime;
Z-(+)-1-Azabicyclo[2.2.1]heptan-3-one, O-(3-(4'-chlorophenyl)-2-propynyl)oxime;
Z-(−)-1-Azabicyclo[2.2.1]heptan-3-one, O-(3-(4'-chlorophenyl)-2-propynyl)oxime;
Z-(±)-1-Azabicyclo[2.2.1]heptan-3-one, O-(3-(2'-fluorophenyl)-2-propynyl)oxime;
Z-(+)-1-Azabicyclo[2.2.1]heptan-3-one, O-(3-(2'-fluorophenyl)-2-propynyl)oxime;
Z-(−)-1-Azabicyclo[2.2.1]heptan-3-one, O-(3-(2'-fluorophenyl)-2-propynyl)oxime;
Z-(±)-1-Azabicyclo[2.2.1]heptan-3-one, O-(3-(3'-fluorophenyl)-2-propynyl)oxime;
Z-(+)-1-Azabicyclo[2.2.1]heptan-3-one, O-(3-(3'-fluorophenyl)-2-propynyl)oxime;
Z-(−)-1-Azabicyclo[2.2.1]heptan-3-one, O-(3-(3'-fluorophenyl)-2-propynyl)oxime;
Z-(±)-1-Azabicyclo[2.2.1]heptan-3-one, O-(3-(4'-fluorophenyl)-2-propynyl)oxime;
Z-(+)-1-Azabicyclo[2.2.1]heptan-3-one, O-(3-(4'-fluorophenyl)-2-propynyl)oxime;
Z-(−)-1-Azabicyclo[2.2.1]heptan-3-one, O-(3-(4'-fluorophenyl)-2-propynyl)oxime;
Z-(±)-1-Azabicyclo[2.2.1]heptan-3-one, O-(Z-3-methyl-5-phenyl-2-penten-4-ynyl)oxime;
Z-(+)-1-Azabicyclo[2.2.1]heptan-3-one, O-(Z-3-methyl-5-phenyl-2-penten-4-ynyl)oxime;
Z-(−)-1-Azabicyclo[2.2.1]heptan-3-one, O-(Z-3-methyl-5-phenyl-2-penten-4-ynyl)oxime;
Z-(±)-1-Azabicyclo[2.2.1]heptan-3-one, O-(E-3-methyl-5-phenyl-2-penten-4-ynyl)oxime;
Z-(+)-1-Azabicyclo[2.2.1]heptan-3-one, O-(E-3-methyl-5-phenyl-2-penten-4-ynyl)oxime;
Z-(−)-1-Azabicyclo[2.2.1]heptan-3-one, O-(E-3-methyl-5-phenyl-2-penten-4-ynyl)oxime;
Z-(±)-1-Azabicyclo[2.2.1]heptan-3-one, O-(Z-3-methyl-2-penten-4-ynyl)oxime;
Z-(+)-1-Azabicyclo[2.2.1]heptan-3-one, O-(Z-3-methyl-2-penten-4-ynyl)oxime;
Z-(−)-1-Azabicyclo[2.2.1]heptan-3-one, O-(Z-3-methyl-2-penten-4-ynyl)oxime;
Z-(±)-1-Azabicyclo[2.2.1]heptan-3-one, O-(E-3-methyl-2-penten-4-ynyl)oxime;
Z-(+)-1-Azabicyclo[2.2.1]heptan-3-one, O-(E-3-methyl-2-penten-4-ynyl)oxime;
Z-(−)-1-Azabicyclo[2.2.1]heptan-3-one, O-(E-3-methyl-2-penten-4-ynyl)oxime;
Z-(±)-1-Azabicyclo[2.2.1]heptan-3-one, O-(3-(3',4'-dimethoxyphenyl)-2-propynyl)oxime;
Z-(+)-1-Azabicyclo[2.2.1]heptan-3-one, O-(3-(3',4'-dimethoxyphenyl)-2-propynyl)oxime;
Z-(−)-1-Azabicyclo[2.2.1]heptan-3-one, O-(3-(3',4'-dimethoxyphenyl)-2-propynyl)oxime;
Z-(±)-1-Azabicyclo[2.2.1]heptan-3-one, O-(3-(4'-methylphenyl)-2-propynyl)oxime;
Z-(+)-1-Azabicyclo[2.2.1]heptan-3-one, O-(3-(4'-methylphenyl)-2-propynyl)oxime;
Z-(−)-1-Azabicyclo[2.2.1]heptan-3-one, O-(3-(4'-methylphenyl)-2-propynyl)oxime;
Z-(±)-1-Azabicyclo[2.2.1]heptan-3-one, O-(3-(3'-methylphenyl)-2-propynyl)oxime;
Z-(+)-1-Azabicyclo[2.2.1]heptan-3-one, O-(3-(3'-methylphenyl)-2-propynyl)oxime;
Z-(−)-1-Azabicyclo[2.2.1]heptan-3-one, O-(3-(3'-methylphenyl)-2-propynyl)oxime;
Z-(±)-1-Azabicyclo[2.2.1]heptan-3-one, O-(3-(2'-methylphenyl)-2-propynyl)oxime;
Z-(+)-1-Azabicyclo[2.2.1]heptan-3-one, O-(3-(2'-methylphenyl)-2-propynyl)oxime;
Z-(−)-1-Azabicyclo[2.2.1]heptan-3-one, O-(3-(2'-methylphenyl)-2-propynyl)oxime;
Z-(±)-1-Azabicyclo[2.2.1]heptan-3-one, O-(3-(4'-trifluoromethylphenyl)-2-propynyl)oxime;
Z-(+)-1-Azabicyclo[2.2.1]heptan-3-one, O-(3-(4'-trifluoromethylphenyl)-2-propynyl)oxime;
Z-(−)-1-Azabicyclo[2.2.1]heptan-3-one, O-(3-(4'-trifluoromethylphenyl)-2-propynyl)oxime;
Z-(±)-1-Azabicyclo[2.2.1]heptan-3-one, O-(3-(3'-trifluoromethylphenyl)-2-propynyl)oxime;
Z-(+)-1-Azabicyclo[2.2.1]heptan-3-one, O-(3-(3'-trifluoromethylphenyl)-2-propynyl)oxime;
Z-(−)-1-Azabicyclo[2.2.1]heptan-3-one, O-(3-(3'-trifluoromethylphenyl)-2-propynyl)oxime;
Z-(±)-1-Azabicyclo[2.2.1]heptan-3-one, O-(3-(2'-trifluoromethylphenyl)-2-propynyl)oxime;
Z-(+)-1-Azabicyclo[2.2.1]heptan-3-one, O-(3-(2'-trifluoromethylphenyl)-2-propynyl)oxime;
   Z-(−)-1-Azabicyclo[2.2.1]heptan-3-one,
O-(3-(2'-trifluoromethylphenyl)-2-propynyl)oxime;
   Z-(±)-1-Azabicyclo[2.2.1]heptan-3-one,
O-(3-phenyl-2-propynyl)oxime;
   Z-(+)-1-Azabicyclo[2.2.1]heptan-3-one,
O-(3-phenyl-2-propynyl)oxime;
   Z-(−)-1-Azabicyclo[2.2.1]heptan-3-one,
O-(3-phenyl-2-propynyl)oxime;
   Z-(±)-1-Azabicyclo[2.2.1]heptan-3-one,
O-(E-3-methyl-5-(3',4'-dichlorophenyl-2-penten-4-ynyl)oxime;
   Z-(+)-1-Azabicyclo[2.2.1]heptan-3-one,
O-(E-3-methyl-5-(3',4'-dichlorophenyl-2-penten-4-ynyl)oxime;
   Z-(−)-1-Azabicyclo[2.2.1]heptan-3-one,
O-(E-3-methyl-5-(3',4'-dichlorophenyl-2-penten-4-ynyl)oxime;
   Z-(±)-1-Azabicyclo[2.2.1]heptan-3-one, O-2-propynyl oxime;
   Z-(+)-1-Azabicyclo[2.2.1]heptan-3-one, O-2-propynyl oxime;
   Z-(−)-1-Azabicyclo[2.2.1]heptan-3-one, O-2-propynyl oxime;
   Z-(±)-1-Azabicyclo[2.2.1]heptan-3-one,
O-(2,5-hexadiynyl)oxime;
   Z-(+)-1-Azabicyclo[2.2.1]heptan-3-one,
O-(2,5-hexadiynyl)oxime;
   Z-(−)-1-Azabicyclo[2.2.1]heptan-3-one,
O-(2,5-hexadiynyl)oxime;
   Z-(±)-1-Azabicyclo[2.2.1]heptan-3-one,
O-(2,5,8-nonatriynyl)oxime;
   Z-(+)-1-Azabicyclo[2.2.1]heptan-3-one,
O-(2,5,8-nonatriynyl)oxime;
   Z-(−)-1-Azabicyclo[2.2.1]heptan-3-one,
O-(2,5,8-nonatriynyl)oxime;
   Z-(±)-1-Azabicyclo[2.2.1]heptan-3-one,
O-(3-(4'-ethoxyphenyl)-2-propynyl)oxime;
   Z-(+)-1-Azabicyclo[2.2.1]heptan-3-one,
O-(3-(4'-ethoxyphenyl)-2-propynyl)oxime;
   Z-(−)-1-Azabicyclo[2.2.1]heptan-3-one,
O-(3-(4'-ethoxyphenyl)-2-propynyl)oxime;
   Z-(±)-1-Azabicyclo[2.2.1]heptan-3-one,
O-(3-(3'-ethoxyphenyl)-2-propynyl)oxime;
   Z-(+)-1-Azabicyclo[2.2.1]heptan-3-one,
O-(3-(3'-ethoxyphenyl)-2-propynyl)oxime;
   Z-(−)-1-Azabicyclo[2.2.1]heptan-3-one,
O-(3-(3'-ethoxyphenyl)-2-propynyl)oxime;
   Z-(±)-1-Azabicyclo[2.2.1]heptan-3-one,
O-(3-(3',4'-methylenedioxyphenyl)-2-propynyl)oxime;
   Z-(+)-1-Azabicyclo[2.2.1]heptan-3-one,
O-(3-(3',4'-methylenedioxyphenyl)-2-propynyl)oxime;
   Z-(−)-1-Azabicyclo[2.2.1]heptan-3-one,
O-(3-(3',4'-methylenedioxyphenyl)-2-propynyl)oxime;
   Z-(±)-1-Azabicyclo[2.2.1]heptan-3-one,
O-(3-(3',4'-dichlorophenyl)-2-propynyl)oxime;
   Z-(+)-1-Azabicyclo[2.2.1]heptan-3-one,
O-(3-(3',4'-dichlorophenyl)-2-propynyl)oxime;
   Z-(−)-1-Azabicyclo[2.2.1]heptan-3-one,
O-(3-(3',4'-dichlorophenyl)-2-propynyl)oxime;
   Z-(±)-1-Azabicyclo[2.2.1]heptan-3-one,
O-(3-(3',5'-dichlorophenyl)-2-propynyl)oxime;
   Z-(+)-1-Azabicyclo[2.2.1]heptan-3-one,
O-(3-(3',5'-dichlorophenyl)-2-propynyl)oxime;
   Z-(−)-1-Azabicyclo[2.2.1]heptan-3-one,
O-(3-(3',5'-dichlorophenyl)-2-propynyl)oxime;
   Z-(±)-1-Azabicyclo[2.2.1]heptan-3-one,
O-(3-(3',5'-bis(trifluoromethyl)phenyl)-2-propynyl)oxime;
   Z-(+)-1-Azabicyclo[2.2.1]heptan-3-one,
O-(3-(3',5'-bis(trifluoromethyl)phenyl)-2-propynyl)oxime;
   Z-(−)-1-Azabicyclo[2.2.1]heptan-3-one,
O-(3-(3',5'-bis(trifluoromethyl)phenyl)-2-propynyl)oxime;
   Z-(±)-1-Azabicyclo[2.2.1]heptan-3-one,
O-(3-(4'-nitrophenyl)-2-propynyl)oxime;
   Z-(+)-1-Azabicyclo[2.2.1]heptan-3-one,
O-(3-(4'-nitrophenyl)-2-propynyl)oxime;
   Z-(−)-1-Azabicyclo[2.2.1]heptan-3-one,
O-(3-(4'-nitrophenyl)-2-propynyl)oxime;
   Z-(±)-1-Azabicyclo[2.2.1]heptan-3-one,
O-(3-(3'-nitrophenyl)-2-propynyl)oxime;
   Z-(+)-1-Azabicyclo[2.2.1]heptan-3-one,
O-(3-(3'-nitrophenyl)-2-propynyl)oxime;
   Z-(−)-1-Azabicyclo[2.2.1]heptan-3-one,
O-(3-(3'-nitrophenyl)-2-propynyl)oxime;
   Z-(±)-1-Azabicyclo[2.2.1]heptan-3-one,
O-(E-3-methyl-5-(4'-methoxyphenyl)-2-penten-4-ynyl)oxime;
   Z-(+)-1-Azabicyclo[2.2.1]heptan-3-one,
O-(E-3-methyl-5-(4'-methoxyphenyl)-2-penten-4-ynyl)oxime;
   Z-(−)-1-Azabicyclo[2.2.1]heptan-3-one,
O-(E-3-methyl-5-(4'-methoxyphenyl)-2-penten-4-ynyl)oxime;
   Z-(±)-1-Azabicyclo[2.2.1]heptan-3-one,
O-(E-3-methyl-5-(3'-methoxyphenyl)-2-penten-4-ynyl)oxime;
   Z-(+)-1-Azabicyclo[2.2.1]heptan-3-one,
O-(E-3-methyl-5-(3'-methoxyphenyl)-2-penten-4-ynyl)oxime;
   Z-(−)-1-Azabicyclo[2.2.1]heptan-3-one,
O-(E-3-methyl-5-(3'-methoxyphenyl)-2-penten-4-ynyl)oxime;
   Z-(±)-1-Azabicyclo[2.2.1]heptan-3-one,
O-(E-3-methyl-5-(2'-methoxyphenyl)-2-penten-4-ynyl)oxime;
   Z-(+)-1-Azabicyclo[2.2.1]heptan-3-one,
O-(E-3-methyl-5-(2'-methoxyphenyl)-2-penten-4-ynyl)oxime;
   Z-(−)-1-Azabicyclo[2.2.1]heptan-3-one,
O-(E-3-methyl-5-(2'-methoxyphenyl)-2-penten-4-ynyl)oxime;
   Z-(±)-1-Azabicyclo[2.2.1]heptan-3-one,
O-(E-3-methyl-5-(3',4'-dimethoxyphenyl)-2-penten-4-ynyl)oxime;
   Z-(+)-1-Azabicyclo[2.2.1]heptan-3-one,
O-(E-3-methyl-5-(3',4'-dimethoxyphenyl)-2-penten-4-ynyl)oxime;
   Z-(−)-1-Azabicyclo[2.2.1]heptan-3-one,
O-(E-3-methyl-5-(3',4'-dimethoxyphenyl)-2-penten-4-ynyl)oxime;
   Z-(±)-1-Azabicyclo[2.2.1]heptan-3-one,
O-(E-3-methyl-5-(3',4',5-trimethoxyphenyl)-2-penten-4-ynyl)oxime;
   Z-(+)-1-Azabicyclo[2.2.1]heptan-3-one,
O-(E-3-methyl-5-(3',4',5-trimethoxyphenyl)-2-penten-4-ynyl)oxime;
   Z-(−)-1-Azabicyclo[2.2.1]heptan-3-one,
O-(E-3-methyl-5-(3',4',5-trimethoxyphenyl)-2-penten-4-ynyl)oxime;
   Z-(±)-1-Azabicyclo[2.2.1]heptan-3-one,
O-(E-3-methyl-5-(4'-methylphenyl)-2-penten-4-ynyl)oxime;
   Z-(+)-1-Azabicyclo[2.2.1]heptan-3-one, O-(E-3-methyl-5-(4'-methylphenyl)-2-penten-4-ynyl)oxime;

Z-(−)-1-Azabicyclo[2.2.1]heptan-3-one, O-(E-3-methyl-5-(4'-methylphenyl)-2-penten-4-ynyl)oxime;

Z-(±)-1-Azabicyclo[2.2.1]heptan-3-one, O-(E-3-methyl-5-(4'-chlorophenyl)-2-penten-4-ynyl)oxime;

Z-(+)-1-Azabicyclo[2.2.1]heptan-3-one, O-(E-3-methyl-5-(4'-chlorophenyl)-2-penten-4-ynyl)oxime;

Z-(−)-1-Azabicyclo[2.2.1]heptan-3-one, O-(E-3-methyl-5-(4'-chlorophenyl)-2-penten-4-ynyl)oxime;

Z-(±)-1-Azabicyclo[2.2.1]heptan-3-one, O-(E-3-methyl-5-(4'-fluorophenyl)-2-penten-4-ynyl)oxime;

Z-(+)-1-Azabicyclo[2.2.1]heptan-3-one, O-(E-3-methyl-5-(4'-fluorophenyl)-2-penten-4-ynyl)oxime; and Z-(−)-1-Azabicyclo[2.2.1]heptan-3-one, O-(E-3-methyl-5-(4'-fluorophenyl)-2-penten-4-ynyl)oxime.

In the process of the instant invention, in Step (a) the alcohol solvent is of sufficient dilution to keep reactants and products in solution. The alcohol solvent is, for example, methanol or ethanol, in a concentration equal to or lower than 0.4M.

The Step (d) of the process of the invention concerns alkylating the oximes in the presence of a basic amine carried out without destroying the stereochemistry of the oxime.

The compounds of the present invention exist in the Z-isomeric form of the oxime, see below, and enantiomeric forms thereof. Moreover, in those compounds in which there is a double bond in a carbon chain, both the Z and E forms of the olefins are included in the present invention.

In the compounds depicted by Formula I, the various substituents are further described as follows. Illustrative examples of straight or branched lower alkyl having from 1 to 4 carbon atoms or from 1 to 6 carbon atoms included methyl, ethyl, n-propyl, isopropyl, n-butyl, tert-butyl, n-pentyl, n-hexyl.

Illustrative of lower alkoxy groups having from 1 to 4 carbon atoms are methoxy, ethoxy, and n-propoxy. Illustrative examples of a saturated straight or branched hydrocarbon chain having from 1 to 20 carbon atoms include n-octyl, n-heptyl, dodecyl, tetradecyl, heptadecyl, etc, and all the illustrative examples of straight or branched lower alkyl groups having from 1 to 6 carbon atoms set forth above.

Illustrative examples of straight or branched unsaturated hydrocarbon chains which contain from 1 to 4 unsaturations which are double or triple bonds are ethenyl, 2,4-pentadienyl, 1,4-pentadienyl, 2,4-pentadiynyl, 1,4-pentadiynyl, 2-penten-4-ynyl, 2-pentyn-4-enyl, 2-propenyl, 3-butenyl, 1-methyl-2-propenyl, 2-pentenyl, 2-octenyl, 5-nonenyl, 4-undecenyl, 2-ethyl-3-butenyl, 4-hexenyl, 9,12-octadienyl, hexadecenyl, ethynyl, 2-propynyl, 1-methyl-2-propynyl, 1-ethyl-2-propynyl, 1-methyl-3-butynyl, 3-butynyl, or 4-pentynyl. Illustrative examples of cycloalkyl groups having from 3 to 6 carbon atoms are cyclopropyl, cyclobutyl, and cyclohexyl.

Pharmaceutically acceptable acid addition salts of the compounds of Formulas I and V are illustratively hydrochloric, sulfuric, phosphoric, acetic, benzoic, citric, malonic, salicylic, malic, fumaric, oxalic, succinic, tartaric, lactic, gluconic, ascorbic, maleic, aspartic, benzenesulfonic, methane and ethanesulfonic, hydroxymethane- and hydroxyethanesulfonic (see, for example, "Pharmaceutical Salts," *J. Pharm. Sci.* 1977;66(1):1–19).

Leaving groups include but are not limited to halogens and arylsulfonyloxy groups.

Inert solvents include but are not limited to N,N-dimethylformamide, tetrahydrofuran, and toluene.

The compounds prepared by the methodology of the present invention are centrally acting muscarinic agents and are thus useful as analgesic agents for the treatment of pain in mammals including man, as sleep aids, and as agents for treating the symptoms of senile dementia, Alzheimer's disease, Huntington's chorea, tardive dyskinesia, hyperkinesia, mania, or similar conditions characterized by decreased cerebral acetylcholine production or release, or conditions that respond favorably to central cholinergic stimulation.

In therapeutic use as agents for treating pain or for treating cerebral insufficiency, the compounds utilized in the pharmaceutical method of this invention are administered to the patient at dosage levels of from 0.07 to 700 mg per day. For a normal human adult of approximately 70 kg of body weight, this translates into a dosage of from 0.01 to 100 mg/kg of body weight per-day. The specific dosages employed, however, may be varied depending upon the requirements of the patient, the severity of the condition being treated, and the activity of the compound being employed. The determination of optimum dosages for a particular situation is within the skill of the art.

For preparing pharmaceutical compositions from the compounds of this invention, inert, pharmaceutically acceptable carriers can be either solid or liquid. Solid form preparations include powders, tablets, dispersible granules, capsules, cachets, and suppositories.

A solid carrier can be one or more substances which may also act is diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active compound is mixed with the carrier having the necessary binding properties in suitable proportions and compacted in the shape and size desired.

For preparing suppositories, a low-melting wax such as a mixture of fatty acid glycerides and cocoa butter is first melted, and the active ingredient is dispersed therein by, for example, stirring. The molten homogeneous mixture is then poured into convenient sized molds and allowed to cool and solidify.

Powders and tablets preferably contain between about 5% to about 70% by weight of the active ingredient. Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The term "preparation" is intended to include the formulation of the active compound with encapsulating material as a carrier providing a capsule in which the active component (with or without other carriers) is surrounded by a carrier, which is thus in association with it. In a similar manner, cachets are also included.

Tablets, powders, cachets, and capsules can be used as solid dosage forms suitable for oral administration.

Liquid form preparations include solutions suitable for oral or parenteral administration, or suspensions, and emulsions suitable for oral administration. Sterile water solutions of the active component or sterile solutions of the active component in solvents comprising water, ethanol, or propylene glycol may be mentioned as examples of liquid preparations suitable for parenteral administration.

Sterile solutions may be prepared by dissolving the active component in the desired solvent system, and then passing the resulting solution through a membrane filter to sterilize it or, alternatively, by dissolving the sterile compound in a previously sterilized solvent under sterile conditions.

Aqueous solutions for oral administration can be prepared by dissolving the active compound in water and adding suitable flavorants, coloring agents, stabilizers, and thickening agents as desired. Aqueous suspensions for oral use can be made by dispersing the finely divided active component in water together with a viscous material such as natural or synthetic gums, resins, methyl cellulose, sodium carboxymethyl cellulose, and other suspending agents known to the pharmaceutical formulation art.

Scheme I below illustrates the preparation of the intermediate used in producing the final products.

SCHEME I

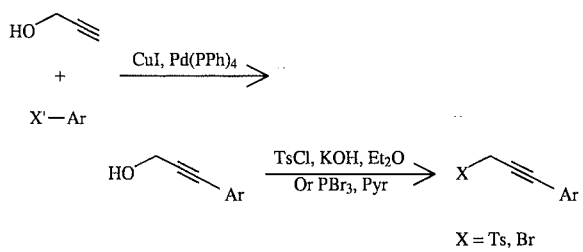

X = Ts, Br

Variations are those that would occur to a skilled artisan or as known in the art.

Scheme II below illustrates the process of the instant invention.

SCHEME II

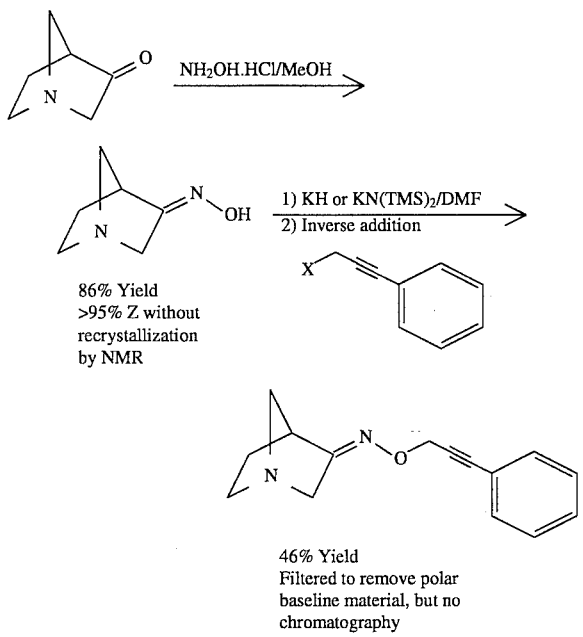

86% Yield
>95% Z without recrystallization by NMR

46% Yield
Filtered to remove polar baseline material, but no chromatography
>98% Z by NMR

EXAMPLE 1

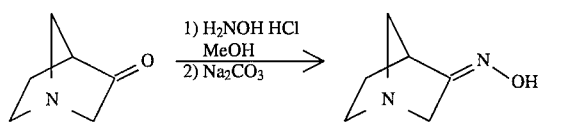

(Z)-1-Azabicyclo[2.2.1]heptan-3-one oxime

A mixture of 1-azabicyclo[2.2.1]heptan-3-one (8.83 g, 79 mmol) and hydroxylamine hydrochloride (5.52 g, 79 mmol) in MeOH (200 mL) was stirred at 25° C. for 18 hours. The solvent was removed under reduced pressure and the tan solid was partitioned between saturated $Na_2CO_3$ and $CHCl_3$. The organic extracts were dried ($Na_2CO_3$), and concentrated to give the oxime, 5.48 g, 54.7%. The aqueous layer was concentrated, and re-extracted with $CHCl_3$ to yield another 3.17 g product. Total yield, 8.65 g, 86%. The ratio is from 95% to 98% Z to E.

Anal. Calc. for $C_6H_{10}N_2O$: C, 57.12; H, 7.99; N, 22.20. Found: C, 56.98; H, 7.87; N, 22.04. MS (m/e, relative intensity): 126 (M+, 32), 109 (100); $^1$H-NMR ($CDCl_3$): δ1.62–1.72 (m, 1H), 1.85–1.98 (m, 1H), 2.55 (dd, J=3.7, 9.8 Hz, 1H), 2.58–2.68 (m, 1H), 2.75 (d, J=9.8 Hz, 1H), 2.92–3.04 (m, 1H), 3.14 (d, J=4.0 Hz, 1H), 3.23 (dd, J=3.5, 17.2 Hz, 1H), 3.51 (dd, J=1.8,,17.2 Hz, 1H).

NOTE: Do not run more concentrated than 0.4M, as the less soluble E-isomer will precipitate out, leading to increased production of the undesired E-isomer.

EXAMPLE 2

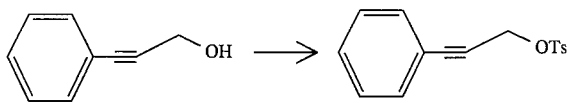

3-Phenyl-2-propynyl-tosylate

To a cooled solution of 3-phenyl-2-propyn-1-ol (5.0 g, 38 mmol) and 4-toluenesulfonyl chloride (8.62 g, 45 mmol) in $Et_2O$ (200 mL) was added powdered KOH (10.66 g, 190 mmol), in portions, over 20 minutes. The reaction was stirred at 0° C. for 5 hours, and was then poured into ice water. The layers were separated, the aqueous layer extracted twice with $Et_2O$, and the combined organics dried ($MgSO_4$). The solvent was removed under reduced pressure, and the solid residue was triturated with hot hexanes. A white solid was filtered, washed with hexanes, and dried to give 3-phenyl-2-propynyl- 1-tosylate, 8.32 g, 76%, mp 76°–78° C.

Anal. Calc. for $C_{16}H_{14}SO_3$: C, 67.11; H, 4.93; S, 11.20. Found: C, 67.15; H, 4.93; S, 10.96. MS (m/e, relative intensity): 286 (M+, 2), 131 (M-$SO_2$Tol, 39), 115 (M—$OSO_2$Tol, 100); $^1$H-NMR ($CDCl_3$): δ2.39 (s, 3H), 4.95 (s, 2H), 7.23–7.35 (m, 7H), 7.85 (dd, J=1.7, 6.5 Hz, 2H).

EXAMPLE 3

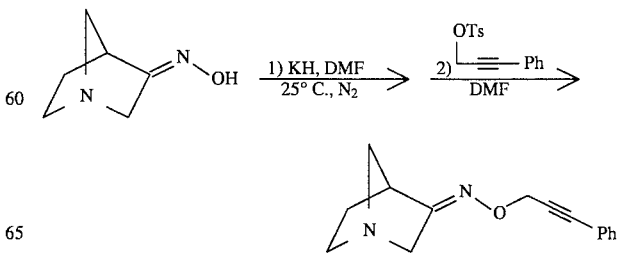

Z-(±)-1-Azabicyclo[2.2.1]heptan, 3-one, O-(3-phenyl- 2-propynyl)oxime

To a suspension of potassium hydride (0.16 g, 4.0 mmol) in DMF (15 mL) was added 1-azabicyclo[ 2.2.1]heptan-3-one oxime (Example 1) (0.50 g, 3.96 mmol) in portions. The anion was stirred for 20 minutes, to form a clear light brown solution. The anion was added dropwise to a solution of 3-phenyl-2-propynyl-tosylate (Example 2) (1.15 g, 4.0 mmol) in DMF (15 mL). The first flask was rinsed with 5 mL of DMF and the solution added to the reaction. The reaction was stirred at 25° C. for 16 hours. The reaction was quenched by careful addition of $H_2O$ (1.5 mL) and the solvent was removed under high vacuum. The residue was dissolved in $CHCl_3$ and filtered through silica gel (95:5 $CHCl_3$:MeOH) to give the product (0.44 g). The free base was dissolved in $Et_2O$ and 1 eq. of oxalic acid in $Et_2O$ was added dropwise. The resulting tan solid was collected through filtration, washed with $Et_2O$, and dried to give 0.42 g of a solid. $^1$H-NMR ($CDCl_3$): δ1.69 (m, 1H), 2.18 (m, 1H), 3.35–3.08 (m, 4H), 3.43 (d, J=Hz, 1H), 3.83 (dd, J=Hz, 1H), 3.98 (dd, J=Hz, 1H), 4.90 (s, 2H), 7.42 (m, 5H). NMR indicated a greater than >98% Z-oxime stereochemistry.

EXAMPLE 4

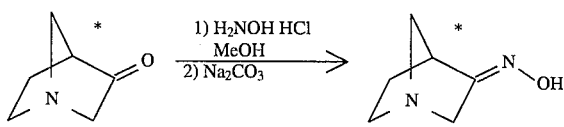

(R)-(Z)-1-Azabicyclo[2.2.1]heptan-3-one oxime

A mixture of (R)-1-azabicyclo[2.2.1]heptan-3-one (U.S. Pat. No. 5,306,718) (2.22 g, 20 mmol) and hydroxylamine hydrochloride (1.39 g, 20 mmol) in MeOH (75 mL) is stirred at 25° C. for 18 hours. The solvent is removed under reduced pressure, the residual solid dissolves in saturated $Na_2CO_3$, and is extracted with $CHCl_3$. The organic extracts are dried ($Na_2CO_3$), and concentrated to give the oxime. The aqueous layer is concentrated, and re-extracted with $CHCl_3$ to yield additional product.

EXAMPLE 5

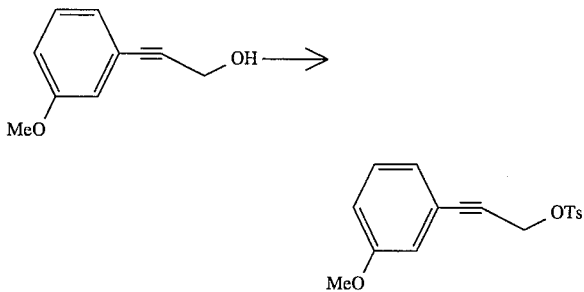

3-(3'-Methoxyphenyl)-2-propynyl-tosylate

To a cooled solution of 3-(3'-methoxyphenyl)-2-propyn-1-ol (13.0 g, 80 mmol) and 4-toluene sulfonyl chloride (18.1 g, 95 mmol) in $Et_2O$ (400 mL) is added powdered KOH (21.28 g, 380 mmol), in portions, over 30 minutes. The reaction is stirred at 0° C. for 5 hours, and is then poured into ice water. The layers are separated, the aqueous layer extracted twice with $Et_2O$, and the combined organics dried ($MgSO_4$). The solvent is removed under reduced pressure, and the solid triturated with hot hexanes. A white solid is filtered, washed with hexanes, and dried to give 3-(3'-methoxyphenyl)-2-propyn- 1-tosylate.

EXAMPLE 6

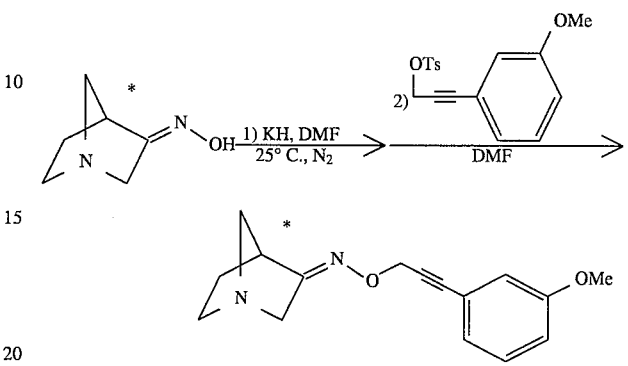

Z-(R)-1-Azabicyclo[2.2.1]heptan-3-one, O-(3-(3'-methoxyphenyl))-2-propynyl)oxime To a suspension of potassium hydride (0.16 g, 4.0 mmol) in DMF (15 mL) is added (R)-1-azabicyclo[ 2.2.1]heptan-3-one oxime (Example 4) (0.50 g, 3.96 mmol) in portions. The anion is stirred for 20 minutes, to form a clear light brown solution. The anion is added dropwise to a solution of 3-(3'-methoxyphenyl)-2-propynyl-tosylate (Example 5) (1.26 g, 4.0 mmol) in DMF (15 mL). The first flask is rinsed with 5 mL of DMF and the solution added to the reaction. The reaction is stirred at 25° C. for 16 hours. The reaction is quenched by careful addition of $H_2O$ (2.5 mL) and the solvent removed under high vacuum. The residue is filtered through silica gel (95:5 $CHCl_3$:MeOH) to give the product. The free base is dissolved in $Et_2O$ and 1 eq. of oxalic acid in $Et_2O$ added dropwise. The resulting tan solid is collected through filtration, washed with $Et_2O$, and dried.

EXAMPLE 7

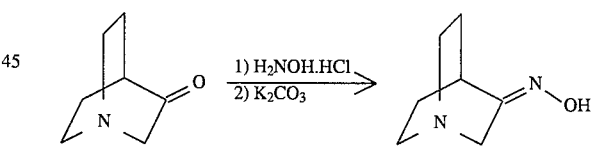

(Z)-1-Azabicyclo[2.2.2]octan-3-one oxime

A mixture of 1-azabicyclo[2.2.2]octan-3-one hydrochloride (3.23 g, 20 mmol) and hydroxylamine hydrochloride (1.40 g, 20 mmol) in MeOH (100 mL) was stirred at 25° C. for 18 hours. The solvent is removed under reduced pressure, aqueous saturated $K_2CO_3$ was added, and the solution extracted with $CHCl_3$. The organic extracts were dried ($MgSO_4$), and concentrated to give the oxime.

NMR and thin layer chromatography showed only starting ketone and a single product. This white solid was dissolved in $CH_2Cl_2$ and chromatographed (flash chromatography, $SiO_2$, 0–5% MeOH/$CHCl_3$) to give a single oxime isomer as a white solid.

Anal. Calc. for $C_6H_{10}N_2O\cdot 0.1M\ H_2O$: C, 59.22; H, 8.66; N, 19.73. Found: C, 59.21; H, 8.28; N, 19.48. MS (m/e, relative intensity): 141 (78), 140 (19), 1233 (100); $^1$H-NMR (CDCl$_3$): δ1.59–1.76 (m, 4H), 2.42 (m, 1H), 2.65–2.82 (m, 4H), 10.23 (s, 1H). $^{13}$C-NMR (CDCl$_3$): δ164.42, 51.82, 47.20, 28.63, 26.32.

The Z-stereochemistry of the isomer was determined by NOE studies.

We claim:

1. A process for the preparation of a compound of formula

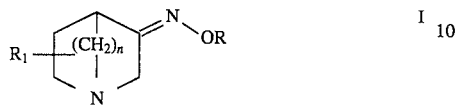   I or a pharmaceutically acceptable acid addition salt thereof and includes racemic as well as enantiomerically pure forms and mixtures thereof wherein n is an integer from 1 to 2;

R$_1$ is hydrogen, a straight or branched lower alkyl group of from 1 to 6 carbon atoms, hydroxy, a straight or branched lower alkoxy group of from 1 to 4 carbon atoms, acyloxy group wherein the acyl moiety has from 2 to 5 carbon atoms, or the group —(CH$_2$)$_m$NR$_{11}$R$_{12}$ wherein m is an integer of from 0 to 4 and R$_{11}$ and R$_{12}$ are the same or different and are hydrogen, a straight or branched lower alkyl of from 1 to 4 carbon atoms, or R$_{11}$ and R$_{12}$ can form a ring of from 3 to 6 atoms;

R is (a) hydrogen;

(b) a straight or branched hydrocarbon chain having from 1 to 20 carbon atoms which is saturated or which is unsaturated and contains from 1 to 4 double and/or triple bonds;

(c) a straight or branched hydrocarbon chain having from 1 to 20 carbon atoms which is saturated or which is unsaturated and contains from 1 to 4 double and/or triple bonds, and the terminal carbon of the hydrocarbon chain is substituted with a group selected from:

(i) a cycloalkyl group having from 3 to 8 carbon atoms or a cycloalkenyl group having from 4 to 8 carbon at ores;

(ii) an aromatic group selected from phenoxy, phenyl, 2- or 3-thienyl, 2- or 3-furanyl, 2- or 3-pyrrolyl, 2-, 3-, or 4-pyridinyl, 3- or 5-(1,2,4)-thiadiazolyl, 3-(1,2,5)-thiadiazolyl, 2-(1,3,4)-thiadiazolyl, 2-triazinyl, 3- or 5-(1,2,4)-oxadiazolyl, 2-(1,3,4)-oxadiazolyl, 3-(1,2,5)-oxadiazolyl, 3- or 5-thiadiazolyl, 2- or 5-pyrimidinyl, 3- or 4-pyridazinyl, 2-, 4-, or 5-thiazolyl, 2-, 4-, or 5-oxazolyl, or 2-pyrazinyl wherein the aromatic group is unsubstituted or is substituted with 1 or 2 substituents selected from straight or branched alkyl having from 1 to 4 carbon atoms, straight or branched alkoxy having from 1 to 4 carbon atoms, chlorine, fluorine, bromine, trifluoromethyl, nitro, hydroxy, trifluoromethoxy, or NR$_4$R$_5$ wherein R$_4$ and R$_5$ have the meanings defined above, (iii) —NR$_6$R$_7$
wherein each of R$_6$ and R$_7$ is hydrogen, alkyl having from 1 to 4 carbon atoms, phenyl or benzyl, or —NR$_6$R$_7$ taken together form a pyrrolidino, piperidino, piperazino, or morpholino ring;

(iv)

wherein R$_6$ and R$_7$ have the meanings defined above;

(v)
wherein R$_8$ is a straight or branched alkyl group having from 1 to 6 carbon atoms;

(vi) CN;

(vii) —CO$_2$R$_9$
wherein R$_9$ is hydrogen, a straight or branched hydrocarbon group having from 1 to 6 carbon atoms which is saturated or which is unsaturated and contains 1 or 2 double and/or triple bonds, or benzyl;

(viii) XR$_{10}$
wherein X is oxygen or sulfur, and R$_{10}$ is a straight or branched hydrocarbon chain having from 1 to 6 carbon atoms which is saturated or which is unsaturated and contains 1 or 2 double and/or triple bonds and is unsubstituted or is substituted with an alkoxy group having from 1 to 4 carbon atoms;

(ix) biphenyl;

(d) the group —CH$_2$CH$_2$CH=C(Ph)$_2$; or (e) the group

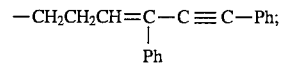

comprising:

(a) stirring a mixture of 1-azabicyclo[2.2.1]heptan-3-one or 1-azabicyclo[2.2.2]octan-3-one or a salt thereof, and hydroxylamine, or a salt thereof, in an alcohol solvent of sufficient dilution to keep reactants and products in solution at a temperature of from 0° C. to 24° C. for from 2 to 48 hours;

(b) removing the solvent, dissolving the remaining product, neutralizing it with base, extracting it into an organic solvent, and drying it to produce the stereochemically pure Z-oxime;

(c) adding the Z-oxime in portions to a suspension of a base with a mono- or dibasic counterion in an aprotic solvent with stirring for from 5 minutes to 5 hours from 0° C. to 50° C. producing the corresponding oxime anion;

(d) adding the product of Step (c) above to a solution of an alkylating agent of Formula R—X, where R is as defined above, and X is a leaving group, in an inert solvent and stirring the mixture at a temperature of from −78° C. to 78° C. for from 10 minutes to 48 hours;

(e) quenching the reaction, removing the solvent and filtering through silica gel to provide the desired specific oxime Z-isomer of Formula I.

2. A process for the preparation of a compound of formula

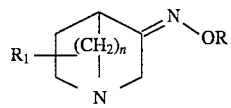

or a pharmaceutically acceptable acid addition salt thereof wherein n is 1;

$R_1$ is hydrogen;

R is a straight or branched hydrocarbon chain having from 1 to 20 carbon atoms which is saturated or which is unsaturated and has from 1 to 4 double and/or triple bonds and the terminal carbon of the hydrocarbon chain is substituted with a group selected from: an aromatic group selected from phenoxy, phenyl, 2- or 3-thienyl, 2- or 3-furanyl, 2- or 3-pyrrolyl, 2-, 3-, or 4-pyridinyl, 3- or 5-(1,2,4)-thiadiazolyl, 3-(1,2,5)-thiadiazolyl, 2-(1,3,4)-thiadiazolyl, 2-triazinyl, 3- or 5-(1,2,4)-oxadiazolyl, 2-(1,3,4)-oxadiazolyl, 3-(1,2,5)-oxadiazolyl, 3- or 5-thiadiazolyl, 2- or 5-pyrimidinyl, 3- or 4-pridazinyl, 2-, 4-, or 5-thiazolyl, 2-, 4-, or 5-oxazolyl, or 2-pyrazinyl wherein the aromatic group is unsubstituted or is substituted with 1 or 2 substituents selected from straight or branched alkyl having from 1 to 4 carbon atoms, straight or branched alkoxy having from 1 to 4 carbon atoms, chlorine, fluorine, bromine, trifluoromethyl, nitro, hydroxy, trifluoromethoxy, or $NR_4R_5$ wherein $R_4$ and $R_5$ have the meanings defined above, comprising:

(a) stirring a mixture of 1-azabicyclo[2.2.1] heptan-3-one or 1-azabicyclo[2.2.2]octan-3-one and hydroxylamine, in an alcohol solvent of sufficient dilution to keep reactants and products in solution at a temperature of from 0° to 24° C. for from 2 to 48 hours;

(b) removing the solvent and dissolving the remaining product, neutralizing it with base, and extracting and drying it to produce the stereochemically pure Z-oxime;

(c) adding the Z-oxime in portions to a suspension of potassium hydride or potassium tert-butoxide or potassium bis(trimethylsilyl) amide in DMF of THF with stirring for from 10 minutes to 2 hours from 0° C. to 30° C. producing the desired oxime anion;

(d) adding the product of Step (c) above to a solution of R—X where R is as defined above, and X is $OSO_2$ Ar or Br, in an inert solvent and stirring the mixture at a temperature of from −10° C. to 50° C. for from 0.5 hours to 18 hours;

(e) quenching the reaction, removing the solvent and filtering through silica gel to provide the desired specific oxime Z-isomer of Formula I.

3. A process according to claim 1 wherein in Step (a) the alcohol solvent is of sufficient dilution to keep reactants and products in solution in a concentration ≦0.4M.

4. A process according to claim 1 wherein in Step (d) the alkylating of the oxime in the presence of a basic amine is carried out without destroying the stereochemistry of the oxime.

5. A process comprising:

(a) stirring a mixture of (+)-1-azabicyclo[2.2.1]heptan-3-one and hydroxylamine hydrochloride in methanol or ethanol at a concentration of ≦0.4M at a temperature of from 0° C. to 24° C. for from 2 to 48 hours;

(b) removing the solvent and dissolving the remaining product in water, increasing the pH with carbonate, and extracting the organic product into $CHCl_3$ and drying the extract to produce the unsubstituted Z-oxime;

(c) adding the Z-oxime in portions to a suspension of potassium hydride or potassium bis(trimethylsilyl)amide or potassium tert-butoxide in DMF or THF with stirring for from 15 minutes to 1 hour at room temperature producing the corresponding oxime anion;

(d) adding the crude reaction mixture from Step (c) to a solution of a compound of Formula R—X, wherein R is (3'-methoxyphenyl)-2-propynyl and X is —$OSO_2$—(p—Me—$C_6H_4$) or bromine in DMF or THF and stirring the mixture at 0° C. to 30° C. for from 1 to 2 hours;

(e) quenching the reaction and removing the solvent, and filtering through silica gel to provide a compound named Z-(−)-1-Azabicyclo[2.2.1]heptan-3-one, O-(3-(3'-methoxyphenyl)-2-propynyl)oxime.

* * * * *